(12) United States Patent
Sakuragi (10) Patent No.: US 9,655,579 B2
(45) Date of Patent: May 23, 2017

(54) IMAGE-BASED DIAGNOSIS ASSISTANCE APPARATUS, METHOD AND PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 426 days.

(21) Appl. No.: 13/755,324

(22) Filed: Jan. 31, 2013

(65) Prior Publication Data

US 2013/0144160 A1 Jun. 6, 2013

Related U.S. Application Data

(63) Continuation of application No. PCT/JP2011/004233, filed on Jul. 27, 2011.

(30) Foreign Application Priority Data

Aug. 11, 2010 (JP) .................................. 2010-180143

(51) Int. Cl.
*A61B 5/05* (2006.01)
*A61B 6/00* (2006.01)
(Continued)

(52) U.S. Cl.
CPC ............ *A61B 6/5217* (2013.01); *A61B 6/032* (2013.01); *A61B 6/037* (2013.01); *A61B 6/461* (2013.01); *A61B 6/469* (2013.01); *A61B 6/507* (2013.01); *A61B 34/10* (2016.02); *G06T 7/0012* (2013.01); *A61B 2034/107* (2016.02);
(Continued)

(58) Field of Classification Search
USPC .................. 600/407, 425; 382/128, 130, 131
See application file for complete search history.

(56) References Cited

U.S. PATENT DOCUMENTS

| | | | |
|---|---|---|---|
| 2009/0010519 A1 | 1/2009 | Wakai et al. | |
| 2011/0188719 A1 | 8/2011 | Ishii | |

FOREIGN PATENT DOCUMENTS

| | | |
|---|---|---|
| JP | 2003-033349 | 2/2003 |
| JP | 2007-054147 | 3/2007 |
| JP | 2009-028515 | 2/2009 |
| WO | WO 2010/013300 | 2/2010 |

OTHER PUBLICATIONS

Machine Translation of JP 2007-054147, Japanese Patent Document having a publication date of Mar. 8, 2007 (actual patent document is cited on IDS as submitted by Applicant). Machine Translation is 12 pages long.*

(Continued)

*Primary Examiner* — James Kish
(74) *Attorney, Agent, or Firm* — Young & Thompson (57) ABSTRACT

A morphology image representing the morphology of a specific organ including a tubular structure in the inside thereof and a function image representing a function level at each position in the organ are obtained. A structure region representing a structure dominating the organ is extracted from the morphology image. A specific partial region in the extracted structure region and a dominated region in the organ are determined, and the dominated region being dominated by a structure in the partial region. In that case, at least one of the partial region determination step and the dominated region determination step is performed by using the function image.

13 Claims, 5 Drawing Sheets

(51) Int. Cl.
*A61B 6/03* (2006.01)
*G06T 7/00* (2017.01)
*A61B 34/10* (2016.01)

(52) U.S. Cl.
CPC ............... *G06T 2207/10072* (2013.01); *G06T 2207/10081* (2013.01); *G06T 2207/10108* (2013.01); *G06T 2207/30056* (2013.01); *G06T 2207/30061* (2013.01); *G06T 2207/30101* (2013.01)

(56) References Cited

OTHER PUBLICATIONS

Hansen et al., "Intraoperative Adaptation and Visualization of Preoperative Risk Analyses for Oncologic Liver Surgery." Proc. SPIE 6918, Medical Imaging 2008: Visualization, Image-guided Procedures, and Modeling, 691809 (Mar. 24, 2008), pp. 1-10.*
Reitinger et al., "Liver Surgery Planning Using Virtual Reality." IEEE Computer Society. Nov./Dec. 2006. pp. 36-47.*
Lange et al., "Augmenting Intraoperative 3D Ultrasound with Preoperative Models for Navigation in Livery Surgery." MICCAI 2004, LNCS 3217, pp. 534-541.*
T. Odagawa, "Kaku Igaku no Saizensen Part 1 Saishin Modality no Rinsho ni Okeru Yuyosei Technical Report Siemens Kaku Igaku Saishin Gijutsu no Shokai", Rad Fan. vol. 6, No. 12, pp. 32-33, Oct. 25, 2008 (Oct. 25, 2008).

* cited by examiner

IMAGE-BASED DIAGNOSIS ASSISTANCE APPARATUS, METHOD AND PROGRAM

BACKGROUND OF THE INVENTION

Field of the Invention

The present invention relates to an image-based diagnosis assistance apparatus, method and program for assisting a doctor in diagnosing an organ, such as a liver and a lung, and in determining a region to be excised in a surgery.

Description of the Related Art

When a surgery for excising a diseased region of an organ, such as a liver and a lung, is performed, it is necessary to appropriately determine a part to be excised before the surgery by performing image-based diagnosis.

Japanese Unexamined Patent Publication No. 2007-054147 (Patent Document 1) proposes an image-based diagnosis assistance apparatus in which blood vessels, hepatic parenchyma, and a tumor part are extracted from an X-ray CT image of a liver. Further, a blood vessel that supplies nutrition to the tumor is identified by identifying, based on the position of a core line of the extracted blood vessel, the diameter of the blood vessel, or the like, a blood vessel the dominated region of which the extracted tumor belongs to, and the region dominated by the blood vessel is displayed as a part to be excised.

Figure 7:
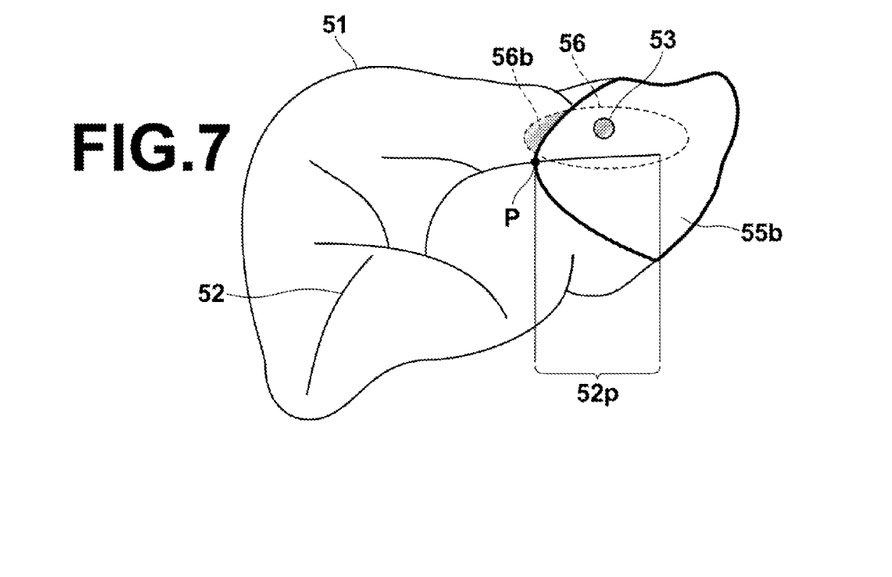
FIG. 7 is a diagram illustrating an example of an image displayed by using a conventional image display method.

Meanwhile, it is desirable that the part to be excised includes a part in which the function of the organ is extremely low, while a normal region is kept as much as possible. For example, as illustrated in FIG. 7, the technique disclosed in Patent Document 1 determines a partial blood vessel 52p (a blood vessel branch from position P to the terminal end) that supplies nutrition to the tumor based on the positional relationship between the blood vessel 52 in the liver and the tumor 53, and determines a dominated region 55b of the partial blood vessel 52p, as apart to be excised. However, since the technique does not pay attention to an evaluation of the function of the organ, the determined excision region 55b does not appropriately include the region to be excised, in which the function is extremely low, in some cases. For example, a region 56b in FIG. 7 is not appropriately included in the region to be excised. In FIG. 7, a region 56 represents a region in which the function of the liver is extremely low.

SUMMARY OF THE INVENTION

In view of the foregoing circumstances, it is an object of the present invention to provide an image-based diagnosis assistance apparatus, method and program that makes it possible to more appropriately determine a part to be excised, considering the function level of an organ.

An image-based diagnosis assistance apparatus of the present invention is an image-based diagnosis assistance apparatus comprising:

an image storage means that stores a morphology image representing the morphology of a specific organ including a tubular structure in the inside thereof and a function image representing a function level at each position in the organ;

a structure region extraction means that extracts a structure region representing the structure dominating the organ from the morphology image;

a partial region determination means that determines a specific partial region in the extracted structure region; and a dominated region determination means that determines a dominated region in the organ, and the dominated region being dominated by a structure in the determined partial region, wherein at least one of the step of determining the partial region by the partial region determination means and the step of determining the dominated region by the dominated region determination means is performed by using the function image.

In the aforementioned apparatus, the dominated region determination means may determine the dominated region by using a distance between each part of the organ and the determined partial region in the morphology image, and the distance having been weighted based on a function level at each position on a shortest path.

Further, the aforementioned apparatus may include a lesion region obtainment means that obtains a lesion region in the organ in the morphology image, and the partial region determination means may determine the partial region in such a manner that the dominated region includes the lesion region obtained by the lesion region obtainment means. This lesion region obtainment means may obtain, as the lesion region, a region of the morphology image located at a position corresponding to a region the function level of which is lower than a predetermined reference value in the function image.

Further, the apparatus may include a specification means that specifies an arbitrary position in the structure region, and the partial region determination means may determine the partial region based on the specified position.

Further, the apparatus may include a lesion region obtainment means that obtains a lesion region in the organ in the morphology image, and the partial region determination means may determine the partial region in such a manner that the dominated region includes the lesion region obtained by the lesion region obtainment means and that an evaluation value calculated by using the function level at each position in a region other than the dominated region becomes the highest.

Further, the apparatus may include a normalization means that normalizes the function level at each position in the organ to a positive or negative value with respect to a predetermined function level set to zero, and the evaluation value may be the sum of the normalized function level at each of positions in the region other than the dominated region.

Further, the apparatus may include a display control means that displays the dominated region, which has been determined by the dominated region determination means, in a distinguishable manner from the other region.

An image-based diagnosis assistance method of the present invention is a method in which processing performed by each means of the image-based diagnosis assistance apparatus is performed by at least one computer.

An image-based diagnosis assistance program of the present invention is a program for causing at least one computer to execute processing performed by each means of the image-based diagnosis assistance apparatus. The program is recorded in a recording medium, such as a CD-ROM and DVD, or recorded in a storage attached to a server computer or in a network storage in such a manner that the program is downloadable, and provided for a user.

Here, the phrase "a function level at each position in the organ" means how normally a tissue at each position in the organ is functioning.

The phrase "a function image representing a function level" widely means an image from which a function level is directly or indirectly obtainable. The function image includes an image directly representing a function level, as the magnitude of a voxel value, an image based on which a function level is indirectly evaluatable by performing predetermined analysis processing, and the like.

The phrase "dominating the organ" means keeping the function of the organ normal by supplying oxygen and nutrition to the organ.

The term "tubular structure" means a structure, for example, such as a blood vessel in a liver when the organ is the liver, and a bronchus in a lung when the organ is the lung.

The "structure region representing the structure" may be identified by coordinate information about each voxel representing the structure. Alternatively, the structure region may be identified by coordinate information about some representative points representing the structure and information about a vector connecting the representative points to each other.

The phrase "specifies an arbitrary position" means specifying an arbitrary position by a mouse, a keyboard, or another input device.

The term "evaluation value" represents a value obtained by evaluating the function of the whole organ, assuming that excision by the dominated region is performed. It is judgeable that the organ after excision functions more normally as the evaluation value is higher.

According to the image-based diagnosis assistance apparatus, method and program of the present invention, a morphology image representing the morphology of a specific organ including a tubular structure in the inside thereof and a function image representing a function level at each position in the organ are obtained. Further, a structure region representing the structure dominating the organ is extracted from the morphology image. Further, the step of determining a specific partial region in the extracted structure region and the step of determining a dominated region in the organ, and the dominated region being dominated by a structure in the partial region, are performed in such a manner that at least one of the partial region determination step and the dominated region determination step is performed by using the function image. Therefore, it is possible to more appropriately determine a dominated region, in other words, a part to be excised, considering the function level of the organ.

In the aforementioned method, apparatus and program, when the dominated region is determined by using a distance between each part of the organ and the determined partial region in the morphology image, and the distance having been weighted based on a function level at each position on a shortest path, it is possible to more appropriately include a part of the organ in which the function of the organ is extremely low in the dominated region (a part to be excised).

Further, when a lesion region in the organ in the morphology image is obtained, and the partial region is determined in such a manner that the dominated region includes the lesion region obtained in the step of obtaining the lesion region and that an evaluation value calculated by using the function level at each position in a region other than the dominated region becomes the highest, it is possible to make the organ after excision of the dominated region function more normally.

DESCRIPTION OF THE PREFERRED EMBODIMENTS

Hereinafter, embodiments of an image-based diagnosis assistance apparatus, method and program of the present invention will be described in detail with reference to drawings.

In each of the following embodiments, an image-based diagnosis assistance apparatus 1 is a computer in which an image-based diagnosis assistance program of each embodiment has been installed. The computer may be a workstation or a personal computer directly operated by a doctor who performs diagnosis. Alternatively, the computer may be a server computer connected to the workstation or the personal computer through a network. The image-based diagnosis assistance program is stored in a recording medium, such as a DVD and a CD-ROM, and distributed, and installed in the computer from the recording medium. Alternatively, the image-based diagnosis assistance program is stored in a storage device of a server computer connected to a network or a network storage in an accessible manner from the outside. The program is downloaded and installed in a computer used by a doctor upon request.

[Embodiment 1]

Figure 1:
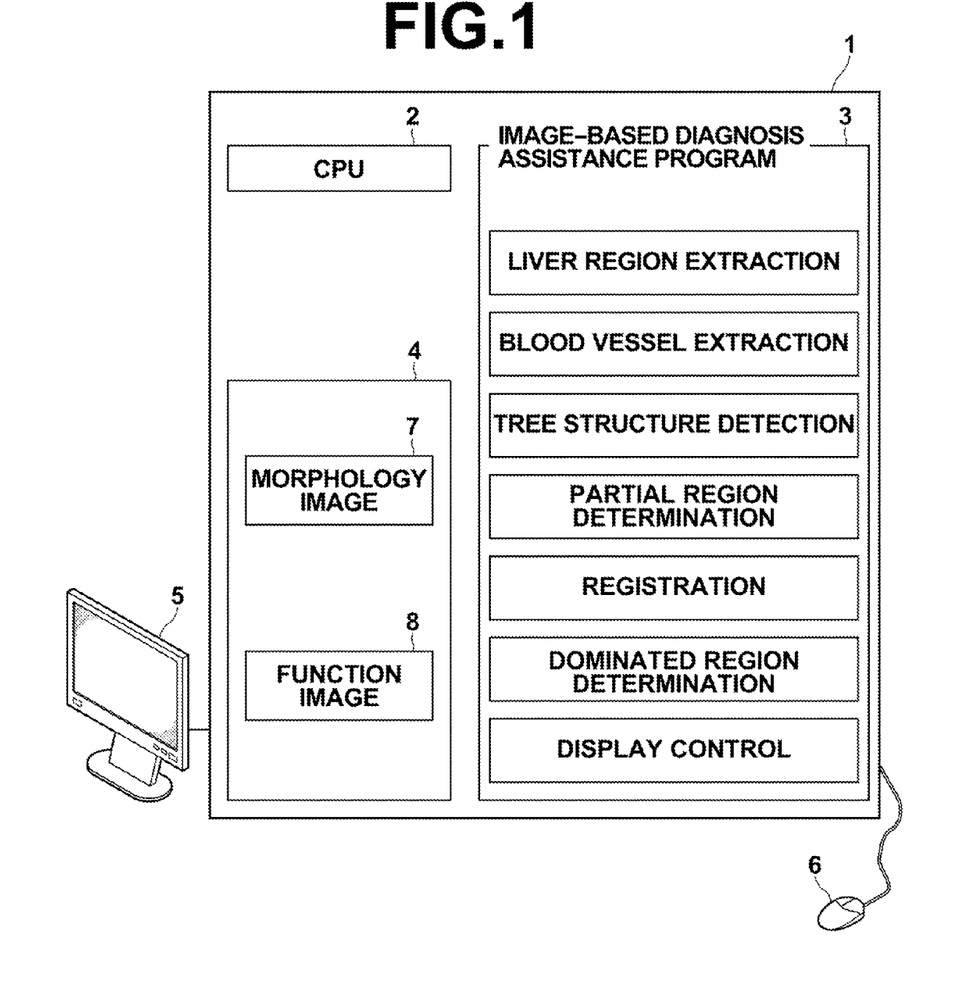
FIG. 1 is a schematic diagram illustrating the configuration of an image-based diagnosis assistance apparatus according to a first embodiment of the present invention.

FIG. 1 is a schematic diagram illustrating the configuration of an image-based diagnosis assistance apparatus realized by installing an image-based diagnosis assistance program in a workstation. As illustrated in FIG. 1, the image-based diagnosis assistance apparatus 1 includes a CPU 2, a memory 3, and a storage (image storage means) 4, as standard workstation configuration. Further, a display 5 and an input device, such as a mouse 6, are connected to the image-based diagnosis assistance apparatus 1.

The storage 4 stores, as a three-dimensional morphology image 7, volume data that have been reconstructed from slice data output from a CT (Computed Tomography) apparatus and an MRI (Magnetic Resonance Imaging) apparatus, volume data output from an MS (Multi Slice) CT apparatus and a cone beam CT apparatus, and the like.

Further, the storage 4 stores, as a three-dimensional function image 8, a SPECT image that has been output from a single photon emission computed tomography (SPECT: Single Photon Emission Computed Tomography) apparatus, and a function image that has been generated by obtaining time-series changes (Time Intensity Curve: TIC) in the density of a contrast agent in an aorta in the abdomen and the hepatic parenchyma by using a dynamic MRI image in which an EOB contrast agent has been used, and by analyzing the time-series changes by deconvolution, and the like.

Further, the memory 3 stores an image-based diagnosis assistance program. The image-based diagnosis assistance program regulates, as processing performed by the CPU 2, liver region extraction processing 11, blood vessel region extraction processing 12, tree structure detection processing 13, partial region determination processing 14, registration processing 15, dominated region determination processing 16, and display control processing 17. When the CPU 2 performs these kinds of processing in accordance with the program, a general-purpose workstation functions as a liver region extraction means, a blood vessel region extraction means, a tree structure detection means, a partial region determination means, a registration means, a dominated region determination means, and a display control means.

Figure 2:
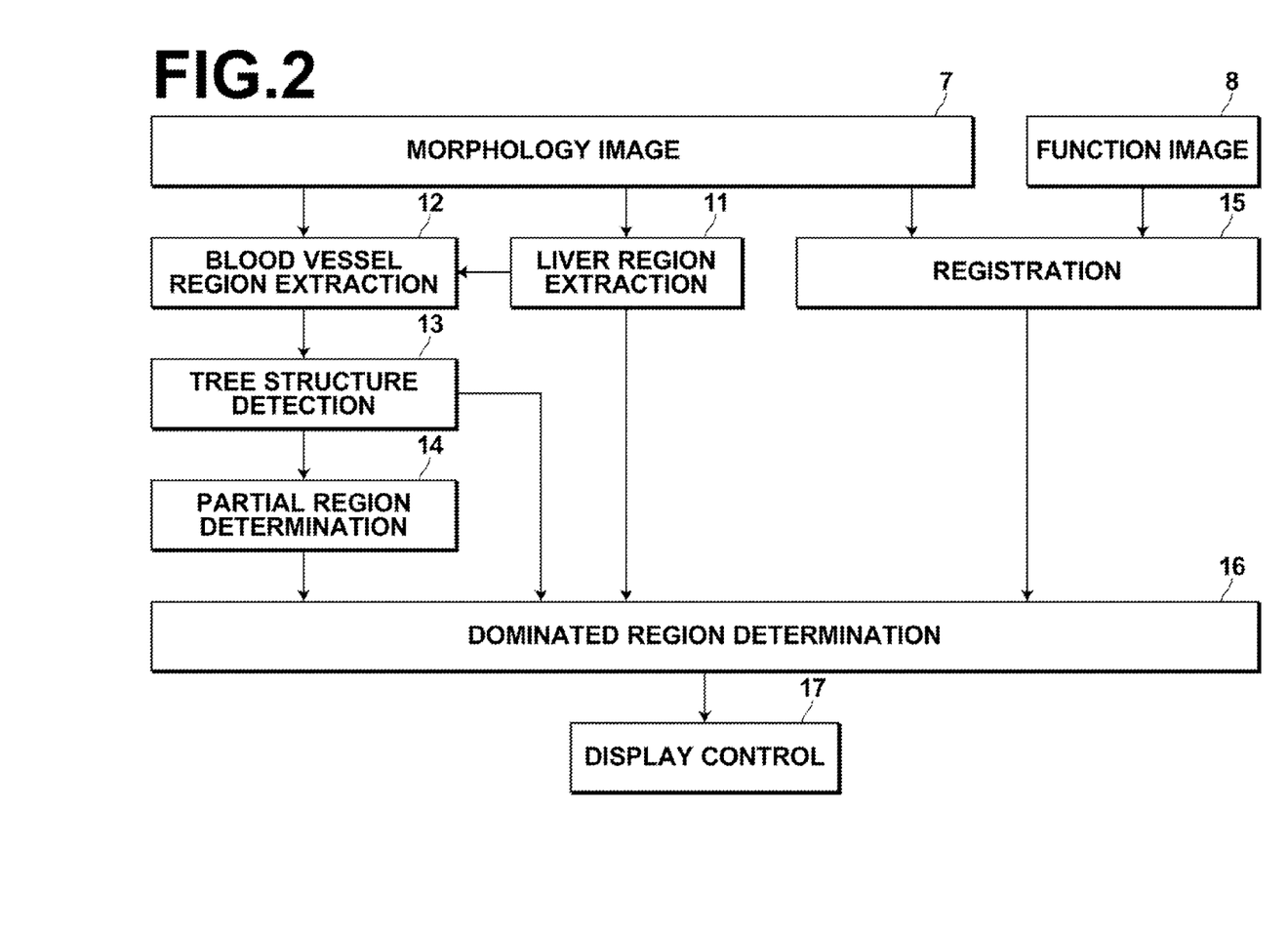
FIG. 2 is a diagram outlining steps performed by the image-based diagnosis assistance apparatus of FIG. 1.

FIG. 2 is a block diagram illustrating a flow of processing performed in accordance with the image-based diagnosis assistance program. First, the image-based diagnosis assistance apparatus 1 displays a list of ID's of subjects to be examined. When the image-based diagnosis assistance apparatus 1 detects a selection operation by a user, the image-based diagnosis assistance apparatus 1 loads an image file related to the selected subject to be examined in the memory 3. A three-dimensional morphology image 7 and a three-dimensional function image 8 that are results of plural kinds of examination (for example, a CT examination and a SPECT examination) performed on the subject to be examined, and which are stored in the storage 4, are loaded in the memory 3.

When the image-based diagnosis assistance apparatus 1 loads the three-dimensional morphology image 7 in the memory 3, first, the image-based diagnosis assistance apparatus 1 performs liver region extraction processing 11 for extracting a liver region 51 on the three-dimensional morphology image 7. Specifically, the image-based diagnosis assistance apparatus 1 calculates a feature value representing a likelihood of the contour of a liver with respect to the value of each voxel data constituting the three-dimensional morphology image 7. Further, the image-based diagnosis assistance apparatus 1 judges whether the voxel data represent the contour of the liver by evaluating the calculated feature value based on an evaluation function that has been obtained in advance by machine learning. Voxel data representing the contour of the whole liver are extracted by repeating this judgment. In the present embodiment, an AdaBoost algorithm is used to obtain the evaluation function. The liver region 51 may be extracted by using another machine learning method, a statistical analysis method, for example, such as a linear discriminant method and neural network, support vector machine, and the like.

Next, the image-based diagnosis assistance apparatus 1 performs blood vessel region extraction processing 12 and tree structure detection processing 13 on the liver region 51 of the three-dimensional morphology image 7 extracted in the liver region extraction processing 11. First, the image-based diagnosis assistance apparatus 1 searches the liver region 51 for a linear structure by calculating eigenvalues of a 3×3 Hessian matrix for each local region in the liver region 51. In a region including a linear structure, one of three eigenvalues of a Hessian matrix is close to 0, and the other two eigenvalues are relatively large. Further, an eigenvector corresponding to the eigenvalue close to 0 indicates the direction of the principal axis of the linear structure. In the blood vessel region extraction processing 12, this relationship is utilized, and a likelihood of a linear structure is judged based on eigenvalues of a Hessian matrix for each local region. With respect to a local region in which a linear structure has been identified, a center point of the local region is detected as a candidate point.

Next, candidate points detected by search are connected to each other based on a predetermined algorithm. Accordingly, a tree structure 52 composed of the candidate points and blood vessel branches (edges) connecting the candidate points to each other is constructed. Coordinate information about the detected plural candidate points and vector information representing the direction of a blood vessel branch are stored in the memory together with identifiers of the candidate points and the blood vessel branches. Then, the contour of a blood vessel (the outer wall of the blood vessel) is identified in a cross section perpendicular to the path of the blood vessel based on values (CT values) of voxels in the vicinity of each detected candidate point. A shape is identified by using a known segmentation technique typified by Group-Cuts. Information necessary to specify an extracted blood vessel region is generated through the processing as described above, and stored in the memory.

In the present embodiment, after the aforementioned procedures have been performed, the image-based diagnosis assistance apparatus 1 outputs the tree structure 52 that has been detected in the tree structure detection processing 13 onto a display screen of the display 5. When a user specifies arbitrary position P on the tree structure 52 by using an input device, such as a mouse 6, the image-based diagnosis assistance apparatus 1 performs partial region determination processing 14 for determining a partial region $52p$ of the blood vessel based on the specified position P. In the present embodiment, a blood vessel branch from the position P that has been specified by the user to the terminal end of the blood vessel branch is determined as the partial region $52p$ in the whole tree structure 51. The result of determination of the partial region $52p$ is stored, as volume data, in the memory 3.

Next, the image-based diagnosis assistance apparatus 1 performs registration processing 15 between the three-dimensional morphology image 7 and the three-dimensional function image 8. Registration of a liver region is performed between the three-dimensional morphology image 7 and the three-dimensional function image 8 by using known rigid or non-rigid registration, and a movement direction and a movement amount of each voxel between the two images are obtained. The coordinate values of the liver region extracted from the three-dimensional function image 8 are transformed by using the movement direction and the movement amount. Accordingly, positions of the same coordinate value in the images represent information at the same position of the liver region. The registration processing 15 may be performed in parallel with the liver region extraction processing 11, the blood vessel region extraction processing 12, the three structure extraction processing 13, and the partial region determination processing 14.

Then, the image-based diagnosis assistance apparatus 1 performs dominated region determination processing 16 for determining a region (dominated region) dominated by a blood vessel of the partial region based on the partial region determined in the partial region determination processing 14. In the present embodiment, the dominated region of the partial region that has been determined in the partial region determination processing 14 is obtained by judging that each point in a region (hepatic parenchyma) other than blood vessels in the liver region is dominated by a blood vessel the distance of which from the point, and the distance having been weighted based on a function level at each position on a shortest path, is the shortest.

Next, with reference to FIG. 3, a method for determining a boundary between dominated regions of two adjacent blood vessels A, B in dominated region determination processing 16 will be described. Here, a case in which the two blood vessels A, B are parallel to each other, and have the same diameter will be used to facilitate understanding. In this case, in each path of an to bn (n=1, 2, 3, . . . ) perpendicular to the principal axes of blood vessels A and B, a point cn that is a boundary between the dominated region of the blood vessel A and the dominated region of the blood vessel B is obtained by the following formula (1). Here, α represents a function level at each position on a shortest path. Plural boundary points obtained in this processing represent boundary line C between the dominated region of the blood vessel A and the dominated region of the blood vessel B.

[Formula 1]

$$\int_{a_n}^{c_n} \alpha \cdot \Delta d = \int_{b_n}^{c_n} \alpha \cdot \Delta d \qquad (1).$$

Figure 3:
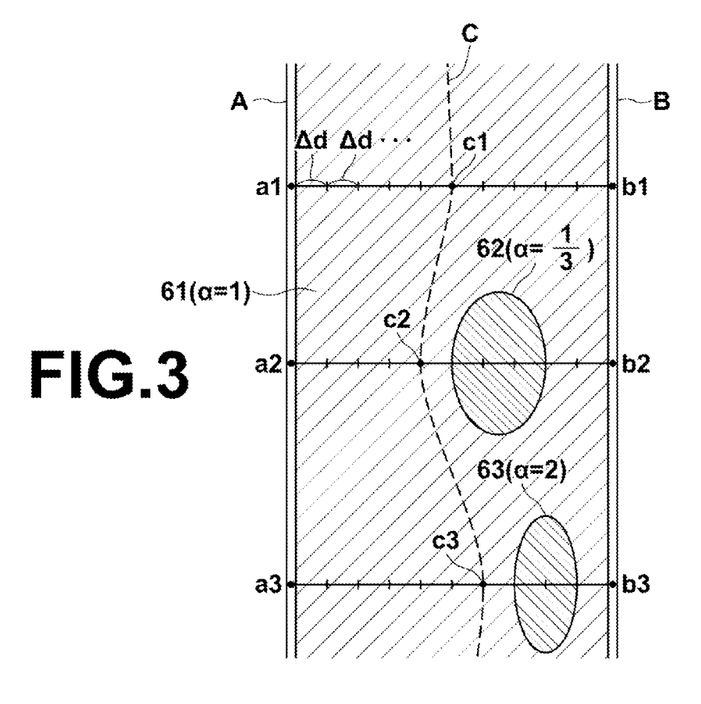
FIG. 3 is a diagram for explaining a method for determining a dominated region.

FIG. 3 illustrates a specific example of boundary points cn determined in three paths an to bn (n=1, 2, 3), in which the distribution of the function level at each position on the path is different from each other, when function level α at each position of a region 61 is 1, function level α in a region 62 is ⅓, and function level α in a region 63 is 2. As illustrated in FIG. 3, the width of the dominated region (a distance from the center line of a blood vessel to the boundary of a dominated region of the blood vessel) depends on the distribution of function levels in the vicinity of the dominated region. Specifically, the width of the dominated region is wide at a position having a part with low function level α in the vicinity of the dominated region, and the width of the dominated region is narrow at a position having a part with high function level α in the vicinity of the dominated region.

Figure 4:
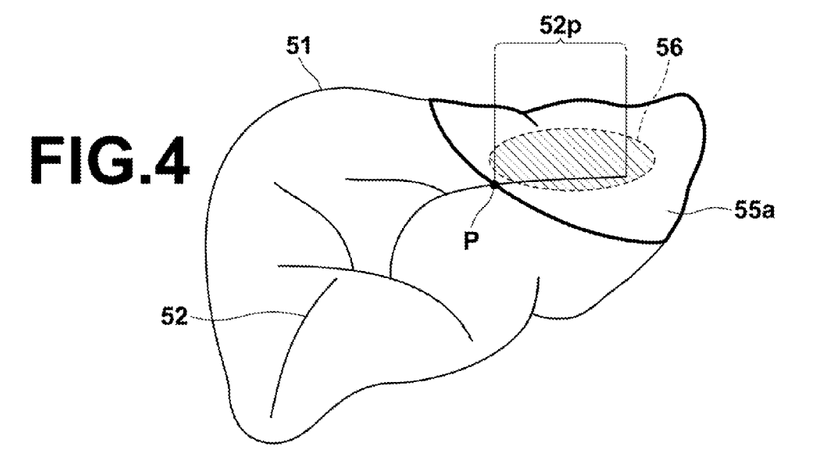
FIG. 4 is a diagram illustrating an example of a determined dominated region.

FIG. 4 is a diagram illustrating an example of a result of the dominated region determination processing 16, which has been described already. Since the boundary line of the dominated region is set by the aforementioned processing, a dominated region 55a of the partial region 52p that has been determined in the partial region determination processing 14 is determined, as illustrated in FIG. 4. The obtained processing result is stored in the memory 3.

Then, the image-based diagnosis assistance apparatus 1 performs display control processing 17. The image-based diagnosis assistance apparatus 1 displays the dominated region 55a that has been determined in the dominated region determination processing 16 on the display screen of the display 5 in such a manner that the dominated region 55a is distinguishable from the other region. The range of the dominated region 55a is presented in a visually distinguishable manner, for example, by assigning different colors to the dominated region 55a and the other region.

As described so far, according to the image-based diagnosis assistance apparatus and program of the present embodiment, the three-dimensional morphology image 7 representing the morphology of a specific liver including a blood vessel in the inside thereof and the three-dimensional function image 8 representing a function level at each position of the liver are obtained. Further, a blood vessel region 52 representing a blood vessel dominating the liver is extracted from the three-dimensional morphology image 7, and a specific partial region 52p in the extracted blood vessel region 52 is determined. Further, a dominated region 55a of the liver, which is dominated by the blood vessel in the partial region 52p, is determined by using the three-dimensional function image 8. Therefore, it is possible to more appropriately determine the dominated region 55a, in other words, a part to be excised, considering function level α of the liver.

Further, in the image-based diagnosis assistance apparatus and program of the present embodiment, specification of arbitrary position P in the blood vessel region 52 is received, and a partial region 52p in the blood vessel region is determined based on the specified position P. Further, a dominated region is determined by using a distance between each part of the liver 51 and the determined partial region 52p in the three-dimensional morphology image 7, and the distance having been weighted based on function level α at each position on a shortest path. Therefore, it is possible to make the dominated region (the part to be excised) 55a include a part in which the function of the liver is extremely low in such a manner that the included part is larger than the case of the dominated region determined by the technique disclosed in Patent Document 1.

In the present embodiment, the case of determining the partial region 52p of the blood vessel based on position P on the tree structure 52 specified by the user was described. However, the present invention is not limited to this case. For example, a lesion region in a liver in a three-dimensional morphology image 7 may be obtained, and a partial region 52p of a blood vessel may be determined in such a manner that a dominated region of the partial region includes the lesion region, and the dominated region being determined by judging that each point in the liver region is dominated by a blood vessel closest to the point.

The processing for obtaining the lesion region may be performed by receiving an input of the position of a lesion, such as a node and a tumor, by a doctor or the like by using an input device, such as a mouse 6, provided in the image-based diagnosis assistance apparatus 1, and the position of the lesion having been detected by the doctor or the like by reading the three-dimensional morphology image 7 or the three-dimensional function image 8. Alternatively, a lesion region may be obtained by automatically detecting a lesion by a computer-aided diagnosis CAD (computer-aided diagnosis) system. For example, a region of the three-dimensional morphology image 7 located at a position corresponding to a region the function level of which is lower than a predetermined reference value in the three-dimensional function image 8 may be obtained as a lesion region.

[Embodiment 2]

Figure 5:
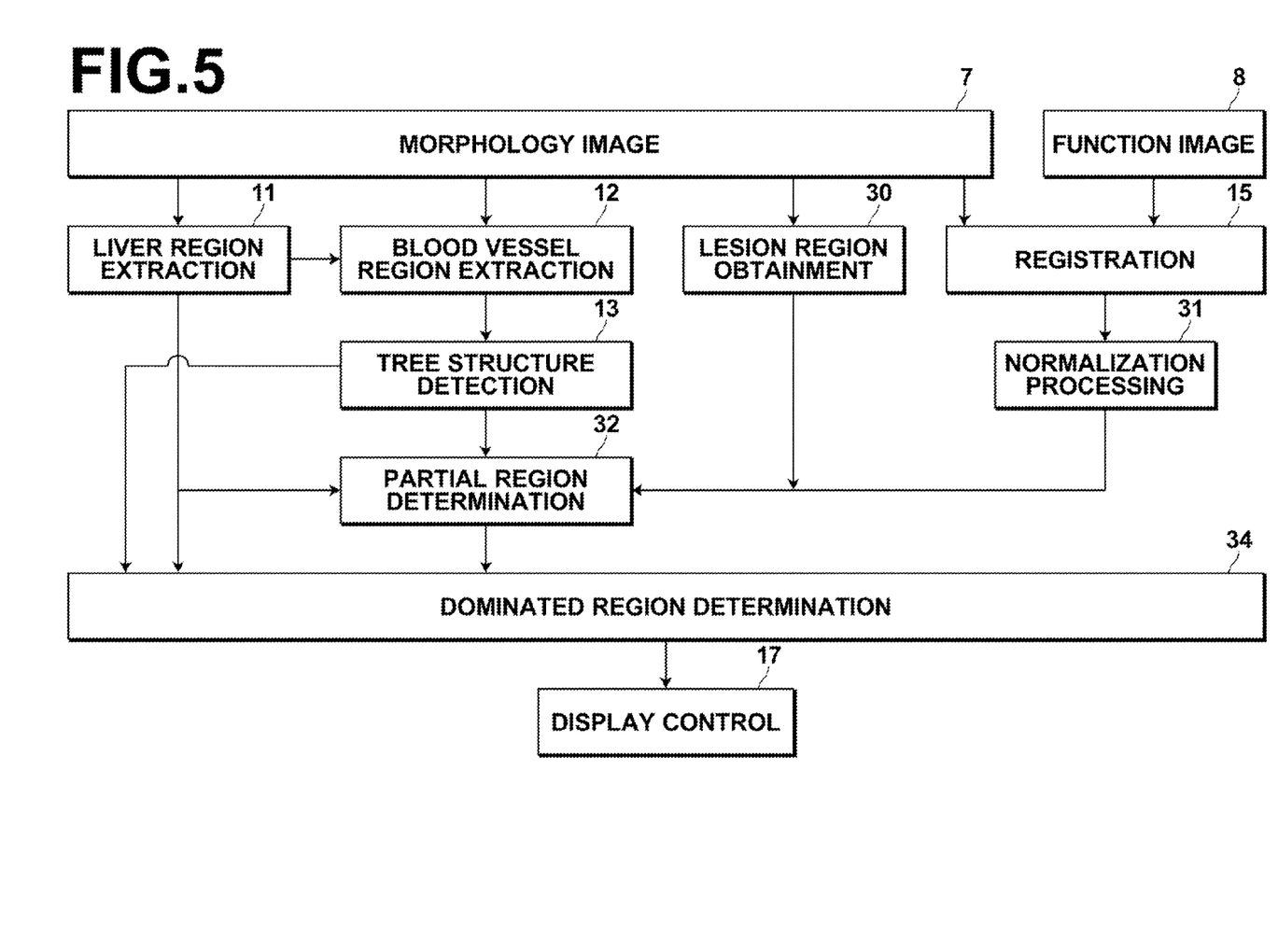
FIG. 5 is a diagram outlining steps performed by an image-based diagnosis assistance apparatus according to a second embodiment.

FIG. 5 is a block diagram illustrating a flow of processing performed by an image-based diagnosis assistance program in a second embodiment. An image-based diagnosis assistance apparatus of the present embodiment differs from the diagnosis apparatus of the first embodiment in that the apparatus of the present embodiment performs lesion region obtainment processing and function level normalization processing before determining a partial region, and the partial region is determined based on the results of processing. Next, different features from the first embodiment will be mainly described, and the same sign will be assigned to the same processing as that of the first embodiment, and the explanation about the same processing will be omitted.

First, lesion region obtainment processing 30 for obtaining a lesion region 53 in the liver in the three-dimensional morphology image 7 will be described. In the lesion region obtainment processing 30, the lesion region 53 is obtained by receiving an input by a doctor or the like by using an input device, such as a mouse 6, provided in the image-based diagnosis assistance apparatus 1. The doctor or the like reads the three-dimensional morphology image 7 or a three-dimensional function image 8 to find a lesion, such as a node and a cancer, and inputs the position of the lesion. Alternatively, the lesion region 53 may be automatically detected by a computer-aided diagnosis CAD (computer-aided diagnosis) system. For example, a region of the three-dimensional morphology image 7 located at a position corresponding to a region the function level of which is lower than a predetermined reference value in the three-dimensional function image 8 may be obtained as the lesion region.

Next, normalization processing 31 for normalizing a function level at each position of the liver will be described. In the normalization processing 31, the value of a function level that is used as a border for judging whether each position of the liver should be excised or not is set to zero. Then, when a voxel value (function level) of the three-dimensional function image 8 is lower than the function level of the border, the function level is normalized to a negative value. When a voxel value (function level) of the three-dimensional function image 8 is higher than the function level of the border, the function level is normalized to a positive value.

Next, partial region determination processing 32 for determining a partial region based on the results of the lesion region obtainment processing 30 and the normalization processing 31 will be described. In the present embodiment, a partial region of a blood vessel is determined in such a manner that the dominated region of the partial region includes the lesion region obtained in the lesion region obtainment processing 30 and that an evaluation value calculated by using the function level at each position in a region other than the dominated region becomes the highest.

Figure 6:
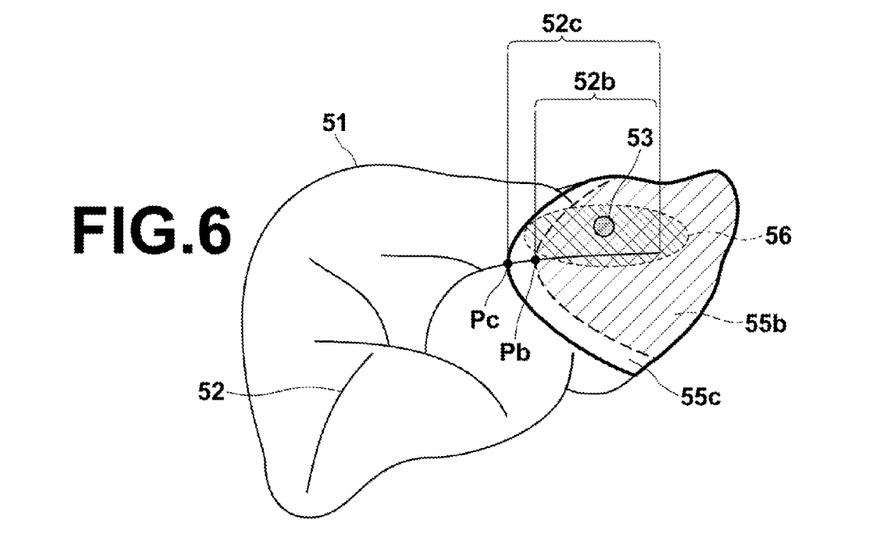
FIG. 6 is a diagram for explaining a method for determining a partial region of a blood vessel.

First, as illustrated in FIG. 6, a blood vessel branch 52b (a blood vessel branch from base point Pb to a terminal end) supplying nutrition to the lesion region 53 is identified by identifying a blood vessel the dominated region of which the extracted lesion region 53 belongs to. Further, a Voronoi diagram is used, and a dominated region 55b of the identified blood vessel is obtained by judging that each point in a region (hepatic parenchyma, or the like) other than blood vessels in the liver region is dominated by a blood vessel closest to each of the points. Further, the sum (evaluation value) of the normalized function level at each of positions in the region other than the dominated region 55b is obtained.

Next, while the base point Pb in the blood vessel branch 52b is moved at predetermined intervals in the upstream downstream direction of the blood vessel, the sum of a normalized function level at each of positions in a region other than the dominated region that is dominated by the blood vessel branch from the position to the terminal end is obtained at each of the positions. Further, point Pc at which the sum is the highest is detected. When the point Pc is detected, a blood vessel branch from the base point Pc to the terminal end is determined as a final partial region 52c.

Next, dominated region determination processing 34 for determining a dominated region of the partial region 52c determined in the partial region determination processing 32 will be described. In the present embodiment, a Voronoi diagram is used, and dominated region 55c of the partial region determined in the partial region determination processing 32 is determined by judging that each point in a region (hepatic parenchyma, or the like) other than blood vessels in the liver region is dominated by a blood vessel closest to each of the points.

As described above, according to the image-based diagnosis assistance apparatus and program of the present embodiment, particularly, a lesion region 53 in a liver 51 in a three-dimensional function image 8 is obtained, and a partial region 52c is determined in such a manner that a dominated region includes the lesion region 53 obtained in lesion region obtainment processing and that an evaluation value calculated by using function level α at each position in a region other than the dominated region is the highest.

Therefore, it is possible to make the liver after excision by the dominated region 55c function more normally.

In each of the aforementioned embodiments, when a shift in position is not present between the three-dimensional morphology image 7 and the three-dimensional function image 8 because imaging is performed under the same imaging conditions, such as a body position during imaging and setting of the coordinate axes of an image to be generated, the aforementioned registration processing is not needed. Then, a function level at each position in the liver region obtained from the three-dimensional function image 8 may be used directly as a function level corresponding to the same coordinate position in the three-dimensional morphology image 7.

In actual excision surgery, a region larger than a predetermined region to be excised tends to be excised because of the characteristic of an excision instrument. Therefore, it is more desirable that a determined dominated region is corrected by setting back a boundary between the determined dominated region and the other region by a predetermined thickness, and that the dominated region after correction is provided for use.

In each of the aforementioned embodiments, a case in which the image-based diagnosis assistance apparatus of the present invention is applied to determination of an excision region of a liver has been described. However, the present invention is not limited to this case. For example, the image-based diagnosis assistance apparatus of the present invention may be applied to a case of determining a region to be excised in another organ including a tubular structure in the inside thereof, such as a lung.

Further, the aforementioned process for determining a region to be excised may be performed further by considering the volume of the morphology of an organ after excision.

What is claimed is:
1. An image-based diagnosis assistance apparatus, comprising:
   a central processor;
   a non-volatile data storage device; and
   a memory device in connection with said central processor, said memory device having stored therein computer-executable instruction code that causes the central processor to operate as:
      an image storage unit that stores a function image, representing a function level at each position in an organ, and a morphology image, representing a morphology of the organ including a tubular structure in an inside thereof;
      a structure region extraction unit configured to extract a structure region representing a structure dominating the organ from the morphology image;
      a partial region determination unit configured to determine and store a specific partial region in the extracted structure region; and
      a dominated region determination unit configured to determine and store a dominated region in the organ, and the dominated region being dominated by a structure in the determined partial region,
   wherein at least one of the determination of the partial region by the partial region determination unit and the determination of the dominated region by the dominated region determination unit is performed using the function image,
   wherein the dominated region determination unit carries out the determination of the dominated region as a function of a distance determined between each part of the organ and the determined partial region in the morphology image, and wherein said distance between each part of the organ and the determined partial region in the morphology image is weighted based on a function level at each position of the organ on a shortest path.

2. The image-based diagnosis assistance apparatus according to claim 1, further comprising:

a lesion region obtainment unit configured to obtain a lesion region in the organ in the morphology image, wherein the partial region determination unit is further configured to determine the partial region so that the dominated region includes the obtained lesion region.

3. The image-based diagnosis assistance apparatus according to claim 2, wherein the lesion region obtainment unit is further configured to obtain, as the lesion region, a region of the morphology image located at a position corresponding to a region the function level of which is lower than a predetermined reference value in the function image.

4. The image-based diagnosis assistance apparatus according to claim 1, further comprising:

a specification unit configured to specify an arbitrary position in the structure region, wherein the partial region determination unit is further configured to determine the partial region based on the specified position.

5. The image-based diagnosis assistance apparatus according to claim 1, further comprising:

a lesion region obtainment unit is further configured to obtain a lesion region in the organ in the morphology image, wherein the partial region determination unit is further configured to determine the partial region so that the dominated region includes the obtained lesion region and so that an evaluation value calculated by using the function level at each position in a region other than the dominated region becomes the highest.

6. The image-based diagnosis assistance apparatus according to claim 5, further comprising:

a normalization unit configured to normalize the function level at each position in the organ to a positive or negative value with respect to a predetermined function level set to zero, wherein the evaluation value is the sum of the normalized function level at each of positions in the region other than the dominated region.

7. The image-based diagnosis assistance apparatus according to claim 1, further comprising:

a display control unit configured to display the determined dominated region so that the determined dominated region is distinguishable from the other region.

8. An image-based diagnosis assistance method to be carried out with a computer device, comprising:

an image obtainment step of reading, into a memory of the computer device, by way of a central processor of the computer device under control of processor-executable instruction code stored in the memory, a function image, representing a function level at each position in an organ, and a morphology image, representing a morphology of the organ including a tubular structure in an inside thereof, from a non-transitory storage medium in communication with the central processor device and in which the function image and the morphology image are stored;

a structure region extraction step of extracting, by way of the central processor device under control of the instruction code stored in the memory, a structure region representing a structure dominating the organ from the morphology image;

a partial region determination step of determining and storing, by way of the central processor device under control of the instruction code stored in the memory, a specific partial region in the extracted structure region; and a dominated region determination step of determining and storing, by way of the central processor device under control of the instruction code stored in the memory, a dominated region in the organ, and the dominated region being dominated by a structure in the determined partial region, wherein at least one of the partial region determination step and the dominated region determination step is performed by using the function image, wherein the dominated region determination step determines the dominated region as a function of a distance determined between each part of the organ and the determined partial region in the morphology image, and wherein said distance between each part of the organ and the determined partial region in the morphology image is weighted based on a function level at each position of the organ on a shortest path.

9. The image-based diagnosis assistance method according to claim 8, wherein the partial region determination step receives specification of an arbitration position in the structure region, and determines the partial region based on the specified position.

10. The image-based diagnosis assistance method according to claim 8, the method comprising:

a lesion region obtainment step of obtaining a lesion region in the organ in the morphology image, wherein the partial region determination step further determines the partial region so that the dominated region includes the obtained lesion region and that an evaluation value calculated by using the function level at each position in a region other than the dominated region becomes the highest.

11. A non-transitory computer-readable medium storing therein an image-based diagnosis assistance program comprising computer-readable instruction code that, upon execution by a central processor device of the computer, causes the computer to function as:

an image storage unit configured to store a morphology image, representing the morphology of a specific organ including a tubular structure in an inside thereof, and a function image, representing a function level at each position in the organ;

a structure region extraction unit configured to extract a structure region representing a structure dominating the organ from the morphology image;

a partial region determination unit configured to determine and store a specific partial region in the extracted structure region; and a dominated region determination unit configured to determine and store a dominated region in the organ, and the dominated region being dominated by a structure in the determined partial region, wherein at least one of the step of determining the partial region by the partial region determination unit and the step of determining the dominated region by the dominated region determination unit is performed by using the function image, wherein the dominated region determination unit determines the dominated region as a function of a distance determined between each part of the organ and the determined partial region in the morphology image, and wherein said distance between each part of the organ and the determined partial region in the morphology image is weighted based on a function level at each position of the organ on a shortest path.

12. The non-transitory computer-readable medium storing therein an image-based diagnosis assistance program according to claim 11, which further causes the computer to function as:

a specification unit configured to specify an arbitrary position in the structure region, wherein the partial region determination unit is further configured to determine the partial region based on the specified position.

13. The non-transitory computer-readable medium storing therein an image-based diagnosis assistance program according to claim 11, which further causes the computer to function as:

a lesion region obtainment unit configured to obtain a lesion region in the organ in the morphology image, wherein the partial region determination unit is further configured to determine the partial region so that the dominated region includes the obtained lesion region and that an evaluation value calculated by using the function level at each position in a region other than the dominated region becomes the highest.

* * * * *